(12) United States Patent
Fancelli et al.

(10) Patent No.: US 7,582,628 B2
(45) Date of Patent: Sep. 1, 2009

(54) PYRROLO[3,4-C]PYRAZOLE DERIVATIVES ACTIVE AS KINASE INHIBITORS, PROCESS FOR THEIR PREPARATION AND PHARMACEUTICAL COMPOSITIONS COMPRISING THEM

(75) Inventors: Daniele Fancelli, Milan (IT); Barbara Forte, Milan (IT); Jürgen Moll, Appiano Gentile (IT); Mario Varasi, Milan (IT); Paola Vianello, Milan (IT)

(73) Assignee: Pfizer Italia S.r.l., Rome (IT)

( * ) Notice: Subject to any disclaimer, the term of this patent is extended or adjusted under 35 U.S.C. 154(b) by 0 days.

(21) Appl. No.: 11/503,256

(22) Filed: Aug. 11, 2006

(65) Prior Publication Data

US 2006/0276471 A1 Dec. 7, 2006

Related U.S. Application Data

(62) Division of application No. 10/882,493, filed on Jul. 1, 2004, now Pat. No. 7,141,568.

(60) Provisional application No. 60/485,814, filed on Jul. 9, 2003.

(51) Int. Cl.
*A61K 31/5375* (2006.01)
*A61K 31/497* (2006.01)
*A61K 31/445* (2006.01)
*C07D 413/10* (2006.01)
*C07D 413/12* (2006.01)
*C07D 401/00* (2006.01)

(52) U.S. Cl. ............................... 514/234.2; 514/254.06; 514/322; 544/140; 544/238; 546/199

(58) Field of Classification Search ............... 514/234.2, 514/254.06, 322; 544/140, 238; 546/199
See application file for complete search history.

(56) References Cited

FOREIGN PATENT DOCUMENTS

| WO | WO 00/69846 | 11/2000 |
|---|---|---|
| WO | WO 01/12188 A1 | 2/2001 |
| WO | WO 01/12189 A1 | 2/2001 |
| WO | WO 02/12242 A2 | 2/2002 |
| WO | WO 02/30927 A1 | 4/2002 |
| WO | WO 02/48114 A1 | 6/2002 |
| WO | WO 02/070515 A2 | 9/2002 |
| WO | WO 03/028720 A1 | 4/2003 |
| WO | WO 2004/014374 A1 | 2/2004 |

OTHER PUBLICATIONS

Keen, et al. , "Aurora-Kinase Inhibitors as Anticancer Agents", Nature Reviews I Cancer, vol. 4, pp. 927-936, Dec. 2004.*
Mol. Cancer. Ther. 2007: 6(12), pp. 3147-3157.*
Mol. Cancer. Ther. 2007: 6(12), pp. 3158-3168.*
Clin. Cancer Res. 2007: 13(12), pp. 3682-3688.*
Clin. Cancer Res. 2006: 12(13), pp. 4080-4089.*
Nat. Med. 2004: 10(3), pp. 262-267.*
Cancer Res. 2005: 65(19), pp. 9038-9046.*
Cohen, Philip. The Development and therapeutic potential of protein kinase inhibitors. Chemical Biology: 3 (1999), 459-465.*
Huff, Joel R. HIV Protease: A novel chemotherapeutic target for AIDS. Journal of Medicinal Chemistry, 34(8) (1991), 2305-2314.*
Golub et al. Science (1999), vol. 286 531-536.*
Lala et al. Cancer and Metastasis Reviews (1998), 17(1), 91-106.*
Tanaka T. et al., "Centrosomal Kinase AIK1 is Overexpressed in Invasive Ductual Carcinoma of the Breast", *Cancer Research* 59:2041-2044 (1999).
Cohen P., "The Development and Therapeutic Potential of Protein Kinase Inhibitors", *Current Opinion of Chemical Biology* 3:459-465 (1999).
Sen S. et al., "Amplification/Overexpression of a Mitotic Kinase Gene in Human Bladder Cancer", *Journal of the National Cancer Institute* 94(17):1320-1329 (2002).
Warner S.L. et al., "Targeting Aurora-2 Kinase in Cancer", *Molecular Cancer Therapeutics* 2:589-595 (2003).
Dermer G.B., "Another Anniversary for the War on Cancer", *Biotechnology* 12:320 (1994).
Freshney R.I., "Culture of Animal Cells", *A Manual of Basic Technique* (1983).

* cited by examiner

*Primary Examiner*—Kamal A Saeed
*Assistant Examiner*—Samantha L Shterengarts
(74) *Attorney, Agent, or Firm*—Scully, Scott, Murphy & Presser, P.C.

(57) ABSTRACT

Pyrrolo[3,4-c]pyrazole derivatives of formula (I) and pharmaceutically acceptable salts thereof, as defined in the specification, process for their preparation and pharmaceutical compositions comprising them are disclosed; the compounds of the invention may be useful, in therapy, in the treatment of diseases associated with a disregulated protein kinase activity, like cancer.

6 Claims, No Drawings

PYRROLO[3,4-C]PYRAZOLE DERIVATIVES ACTIVE AS KINASE INHIBITORS, PROCESS FOR THEIR PREPARATION AND PHARMACEUTICAL COMPOSITIONS COMPRISING THEM

CROSS REFERENCE TO RELATED APPLICATION

The present application is a divisional of application Ser. No. 10/882,493 filed on Jul. 1, 2004 now U.S. Pat. No. 7,141,568 which claims benefit of U.S. Provisional Application No. 60/485,814 filed Jul. 9, 2003.

BACKGROUND OF THE INVENTION

1. Field of the Invention

The present invention relates to pyrrolo-pyrazole derivatives, to a process for their preparation, to pharmaceutical compositions comprising them, and to their use as therapeutic agents, particularly in the treatment of cancer and cell proliferation disorders.

2. Discussion of the Background

The malfunctioning of protein kinases (PKs) is the hallmark of numerous diseases. A large share of the oncogenes and proto-oncogenes involved in human cancers code for PKs. The enhanced activities of PKs are also implicated in many non-malignant diseases, such as benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

PKs are also implicated in inflammatory conditions and in the multiplication of viruses and parasites. PKs may also play a major role in the pathogenesis and development of neurodegenerative disorders.

For a general reference to PKs malfunctioning or disregulation see, for instance, Current Opinion in Chemical Biology 1999, 3, 459-465.

Among the several protein kinases known in the art as being implicated in the growth of cancer cells are Aurora kinases, in particular Aurora-2.

Aurora-2 was found to be over-expressed in a number of different tumor types. Its gene locus maps at 20q13, a chromosomal region frequently amplified in many cancers, including breast [Cancer Res. 1999, 59(9), 2041-4] and colon.

20q13 amplification correlates with poor prognosis in patients with node-negative breast cancer and increased Aurora-2 expression is indicative of poor prognosis and decreased survival time in bladder cancer patients [J. Natl. Cancer Inst., 2002, 94(17), 1320-9]. For a general reference to Aurora-2 role in the abnormal centrosome function in cancer see also Molecular Cancer Therapeutics, 2003, 2, 589-595.

SUMMARY OF THE INVENTION

It is an object of the invention to provide compounds, which are useful in therapy as agents against a host of diseases caused by and/or associated to a disregulated protein kinase activity and, more particularly, Aurora kinases activity.

It is another object to provide compounds, which are endowed with protein kinase inhibiting activity and, more particularly, Aurora kinases inhibiting activity.

The present inventors have now discovered that some pyrrolo-pyrazoles, and derivatives thereof, are endowed with protein kinase inhibiting activity, e.g. Aurora kinases inhibiting activity.

More specifically, the compounds of this invention are useful in the treatment of a variety of cancers including, but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage, including leukemia, acute lymphocitic leukemia, acute lymphoblastic leukemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

Due to the key role of PKs and Aurora kinases in the regulation of cellular proliferation, these pyrrolo-pyrazoles are also useful in the treatment of a variety of cell proliferative disorders such as, for instance, benign prostate hyperplasia, familial adenomatosis, polyposis, neuro-fibromatosis, psoriasis, vascular smooth cell proliferation associated with atherosclerosis, pulmonary fibrosis, arthritis glomerulonephritis and post-surgical stenosis and restenosis.

Accordingly, in a first embodiment, the present invention provides a method for treating cell proliferative disorders caused by and/or associated with an altered protein kinase activity, which comprises administering to a mammal in need thereof an effective amount of a compound of formula (I)

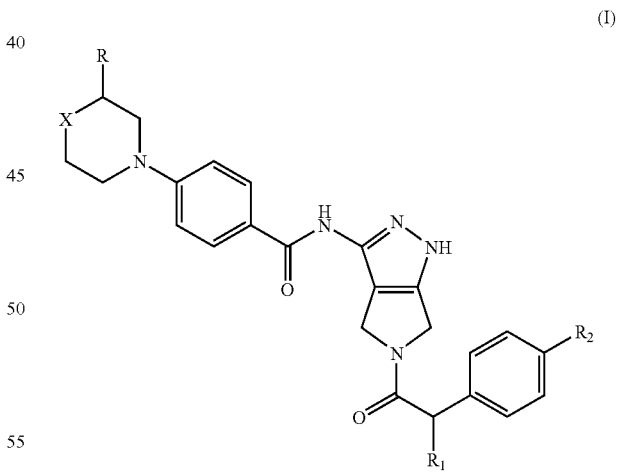

wherein

R is hydrogen or methyl;

$R_1$ is hydroxy or a straight or branched $C_1$-$C_3$ alkyl or alkoxy group;

$R_2$ is a hydrogen or halogen atom;

X is a divalent group selected from methylene (—$CH_2$—) or fluoromethylene (—CHF—), or it is a heteroatom or heteroatomic group selected from oxygen (—O—) or nitrogen (—NR'—) wherein R' is a hydrogen atom, a straight or branched $C_1$-$C_4$ alkyl group or a $C_3$-$C_6$ cycloalkyl group;

or a pharmaceutically acceptable salt thereof.

The above method enables treatment of cell proliferative disorders caused by and/or associated with altered Aurora kinases activity.

In a preferred embodiment of the method described above, the cell proliferative disorder is cancer.

Specific types of cancer that may be treated include carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderma pigmentosum, keratoxanthoma, thyroid follicular cancer, and Kaposi's sarcoma.

The present invention also provides a compound of formula (I)

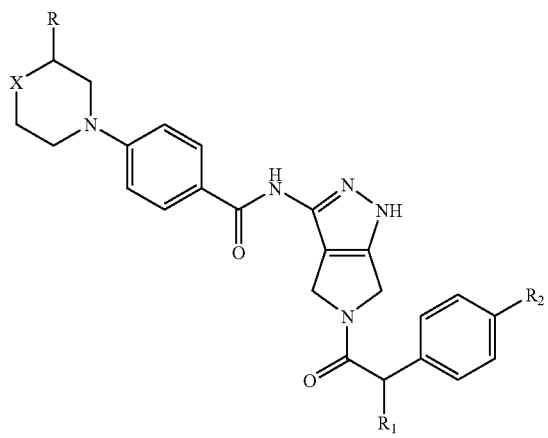

wherein

R is hydrogen or methyl;

$R_1$ is hydroxy or a straight or branched $C_1$-$C_3$ alkyl or alkoxy group;

$R_2$ is a hydrogen or halogen atom;

X is a divalent group selected from methylene (—$CH_2$—) or fluoromethylene (—CHF—), or it is a heteroatom or heteroatomic group selected from oxygen (—O—) or nitrogen (—NR'—) wherein R' is a hydrogen atom, a straight or branched $C_1$-$C_4$ alkyl group or a $C_3$-$C_6$ cycloalkyl group;

or a pharmaceutically acceptable salt thereof.

The present invention also includes methods of synthesizing the pyrrolo-pyrazoles of formula (I) and the pharmaceutically acceptable salts, as well as the pharmaceutical compositions comprising them.

A more complete appreciation of the invention and many of the attendant advantages thereof will be readily obtained as the same becomes better understood by reference to the following detailed description.

DETAILED DESCRIPTION OF THE INVENTION

Several heterocyclic compounds are known in the art as protein kinase inhibitors.

Among them, 3-carboxamido-pyrazoles and 3-ureido-pyrazoles and derivatives thereof, have been disclosed as protein kinase inhibitors in the international patent applications WO 01/12189, WO 01/12188, WO 02/48114 and WO 02/70515, all in the name of the applicant itself.

Fused bicyclic compounds comprising pyrazole moieties and possessing kinase inhibitory activity have been also disclosed in WO 00/69846, WO 02/12242 as well as WO 03/028720 and still unpublished PCT/EP03/04862 application (claiming priority from U.S. patent application 60/381,092, filed in May 17, 2002), all in the name of the applicant itself.

In addition to the above, aminophenyl-piperazine or aminophenyl-piperidine derivatives as possessing inhibitory activity towards prenyl transferase proteins are disclosed in WO 02/30927 in the name of Pierre Fabre Medicament.

The compounds of the present invention fall within the scope of the general formula of the aforementioned WO 02/12242, herewith incorporated by reference, but are not specifically exemplified therein.

The compounds of formula (I) of the invention have asymmetric carbon atoms and may therefore exist as individual optical isomers, as racemic mixtures or as any other mixture comprising a majority of one of the two optical isomers, which are all to be intended as within the scope of the present invention.

Likewise, the use as an antitumor agent of all the possible isomers and their admixtures and of both the metabolites and the pharmaceutically acceptable bio-precursors (otherwise referred to as pro-drugs) of the compounds of formula (I) are also within the scope of the present invention.

Prodrugs are any covalently bonded compounds, which release the active parent drug, according to formula (I), in vivo.

In cases when compounds may exist in tautomeric forms, each form is contemplated as being included within this invention whether existing in equilibrium or predominantly in one form.

As such, unless otherwise provided, when only one of the following tautomeric forms of formula (Ia) or (Ib) is indicated, the remaining one has still to be intended as comprised within the scope of the invention:

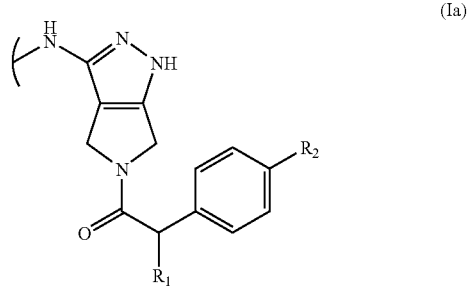

(Ia)

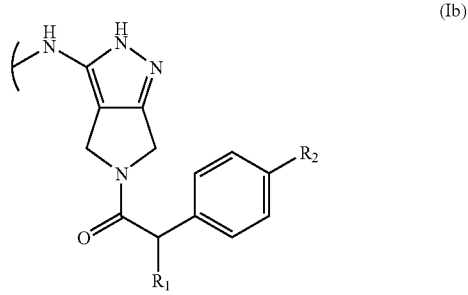

(Ib)

In the present description, unless otherwise specified, with the term straight or branched $C_1$-$C_3$ or $C_1$-$C_4$ alkyl we intend any of the groups such as, for instance, methyl, ethyl, n-propyl, isopropyl, n-butyl, isobutyl, tert-butyl and sec-butyl.

With the term straight or branched $C_1$-$C_3$ alkoxy we intend any of the groups such as, for instance, methoxy, ethoxy, n-propoxy and isopropoxy.

With the term halogen atom we intend a fluorine, chlorine, bromine or iodine atom.

With the term $C_3$-$C_6$ cycloalkyl we intend any group such as cyclopropyl, cyclobutyl, cyclopentyl or cyclohexyl.

Clearly, depending upon the nature of the X group, this same heterocycle being linked to the phenylene moiety of the compounds of formula (I) may represent a piperidino, 4-fluoropiperidino, piperazino, 4-alkyl-piperazino, 4-cycloalkyl-piperazino or morpholino ring.

Pharmaceutically acceptable salts of the compounds of formula (I) include the acid addition salts with inorganic or organic acids such as, for instance, nitric, hydrochloric, hydrobromic, sulfuric, perchloric, phosphoric, acetic, trifluoroacetic propionic, glycolic, lactic, oxalic, malonic, malic, maleic, tartaric, citric, benzoic, cinnamic, mandelic, methanesulphonic, isethionic and salicylic acid.

A preferred class of compounds of the invention is represented by the derivatives of formula (I) wherein R is hydrogen or methyl; $R_1$ is selected from hydroxy, methyl or methoxy; $R_2$ is a hydrogen or fluorine atom; X is selected from methylene, fluoromethylene, —O— or —NR', wherein R' is as above reported.

For a reference to any specific compound of formula (I) of the invention, optionally in the form of a pharmaceutically acceptable salt, see the experimental section and claims.

As formerly indicated, a further object of the present invention is represented by the process for preparing the compounds of formula (I) and the pharmaceutically acceptable salts thereof, which process comprises:

a) reacting a compound of formula (II) with a compound of formula (III)

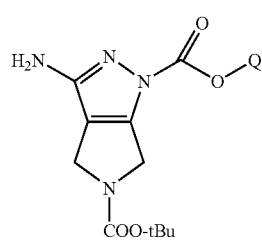

(II)

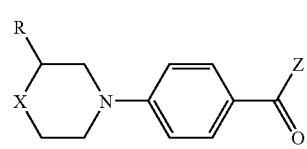

(III)

wherein R and X are as above defined, Q is a lower alkyl group, t-Bu represents tert-butyl and Z is hydroxy or a suitable leaving group, so as to obtain a compound of formula (IV)

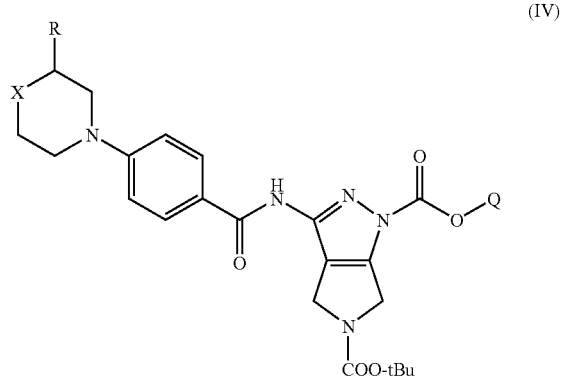

(IV)

b) reacting the compound of formula (IV) under acidic conditions so as to obtain a compound of formula (V)

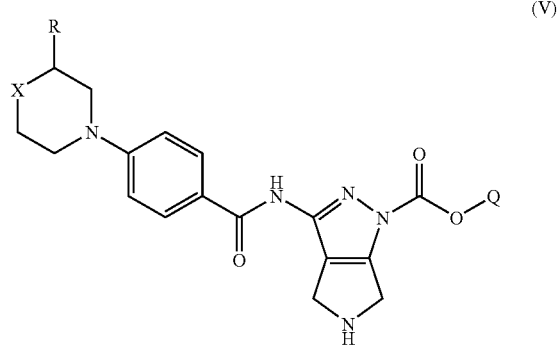

(V)

c) reacting the compound of formula (V) with a compound of formula (VI)

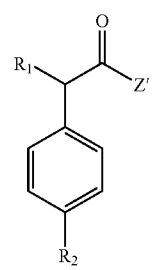

(VI)

wherein $R_1$ and $R_2$ are as above defined and Z' represents hydroxy or a suitable leaving group, so as to obtain a compound of formula (VII)

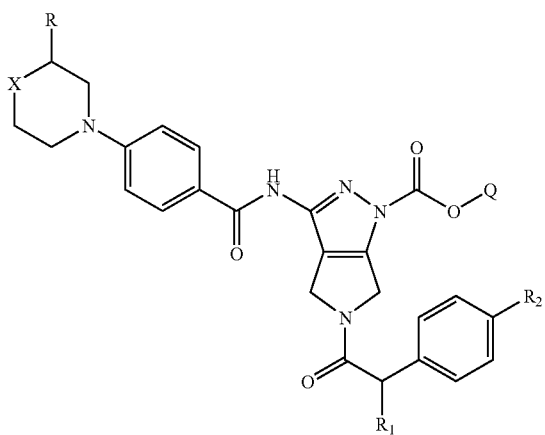

d) reacting the compound of formula (VII) under basic conditions so as to obtain the corresponding compound of formula (I) and, if desired, converting it into a pharmaceutically acceptable salt thereof.

The above process is an analogy process, which can be carried out by working according to very well-known operative conditions.

According to step (a) of the process, the reaction between the compounds of formula (II) and (III) can be carried out in a variety of ways, according to conventional methods for acylating amino derivatives. As an example, the compound of formula (II) may be reacted with an acyl chloride of formula (III) wherein Z represents, as a suitable leaving group, a chlorine atom.

Preferably, this reaction is carried out at a temperature ranging from room temperature to about 60° C., in a suitable solvent such as, for instance, tetrahydrofuran or dichloromethane, and in the presence of a proton scavenger such as triethylamine or diisopropylethylamine. Within the compounds of formula (II) Q represents a lower alkyl group, for instance a $C_1$-$C_4$ alkyl group, more preferably methyl or ethyl.

According to step (b) of the process, the compound of formula (IV) is easily deprotected at the pirrolidine nitrogen atom, by acidic treatment.

This reaction can be conveniently carried out in the presence of a mineral or organic acid such as, for instance, hydrochloric, trifluoroacetic or methansulfonic acid, in a suitable solvent such as dichloromethane, 1,4-dioxane, a lower alcohol (e.g. methanol or ethanol), at a temperature ranging from room temperature to about 40° C. and for a time varying from about 1 hour to about 48 hours.

The compound of formula (V) thus obtained is further reacted, according to step (c) of the process, with a compound of formula (VI). From the above it is clear to the skilled person that also this acylation reaction may be accomplished in a variety of ways and operative conditions, which are widely known in the art for the preparation of carboxamides.

The reaction between a compound of formula (V) and a carboxylic acid of formula (VI) wherein Z' is hydroxy can be carried out in the presence of a coupling agent such as, for instance, carbodiimide, i.e. 1,3-dicyclohexylcarbodiimide, 1,3-diisopropylcarbodiimide, 1-(3-dimethylaminopropyl)-3-ethylcarbodiimide, N-cyclohexylcarbodiimide-N'-propyloxymethyl polystyrene or N-cyclohexylcarbodiimide-N'-methyl polystyrene, in a suitable solvent such as, for instance, dichloromethane, chloroform, tetrahydrofuran, diethyl ether, 1,4-dioxane, acetonitrile, toluene, or N,N-dimethylformamide at a temperature ranging from about −10° C. to reflux for a suitable time, i.e. from about 30 minutes to about 96 hours. The said reaction is optionally carried out in the presence of a suitable catalyst, for instance 4-dimethylaminopyridine, or in the presence of a further coupling reagent such as N-hydroxybenzotriazole.

The reaction between a compound of formula (V) and a compound of formula (VI) can be also carried out, for example, through a mixed anhydride method, by using an alkyl chloroformate, such as ethyl, iso-butyl, or iso-propyl chloroformate, in the presence of a tertiary base, such as triethylamine, N,N-diisopropylethylamine or pyridine, in a suitable solvent such as, for instance, toluene, dichloromethane, chloroform, tetrahydrofuran, acetonitrile, diethyl ether, 1,4-dioxane, or N,N-dimethylformamide, at a temperature ranging from about −30° C. to room temperature.

The reaction between a compound of formula (V) and a carboxylic derivative of formula (VI) wherein Z' is a suitable leaving group can be carried out in the presence of a tertiary base such as triethylamine, N,N-diisopropylethylamine or pyridine, in a suitable solvent, such as toluene, dichloromethane, chloroform, diethyl ether, tetrahydrofuran, acetonitrile, or N,N-dimethylformamide, at a temperature ranging from about −10° C. to reflux.

The compounds of formula (VI) are characterised by the presence of an asymmetric carbon atom being linked to $R_1$ and presently noted with an asterisk

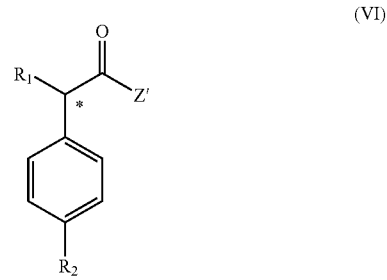

Hence, the compounds of formula (VI) may be either in the form of single enantiomers or as mixtures thereof, also comprehensive of racemic mixtures.

Clearly, depending upon the nature of the compound of formula (VI) being used in the process of the invention, corresponding compounds of formula (VII) having a properly defined stereochemistry at this same carbon atom could be thus obtained.

According to a preferred embodiment of the invention, step (c) is carried out by reacting a suitable compound of formula (VI), which is in a given enantiomeric form.

Likewise, if racemic mixtures of the compound of formula (VI) are employed and whenever final compounds of formula (I) in optical pure form are desired, optical resolution of the intermediate compound of formula (VII) or, alternatively, of the final compound of formula (I) will be required, by working according to conventional means. Just as an example, conventional techniques for racemate resolution include, for instance, partitioned crystallization of diastereoisomeric salt derivatives or preparative chiral HPLC.

Finally, according to step (d) of the process, the compound of formula (VII) is deprotected at the pyrazole nitrogen atom by working according to conventional methods enabling, for instance, the selective hydrolysis of the carbamate group.

As an example, this reaction may be carried out under basic conditions, for instance in the presence of sodium, potassium or lithium hydroxide, or a tertiary amine such as triethylamine, and in a suitable solvent such as N,N-dimethylformamide, methanol, ethanol, tetrahydrofuran, water and mixtures thereof. Typically, the reaction is carried out at temperatures ranging from room temperature to about 60° C. and for a time varying from about 30 minutes to about 96 hours.

Finally, pharmaceutically acceptable salts of the compounds of formula (I) or, alternatively, the free compounds from their salts thereof may be all obtained according to conventional methods.

The starting material of the process of the invention are known or easily prepared according to known methods.

As an example, the preparation of the compound of formula (II) wherein Q represents ethyl is disclosed in the aforementioned international patent application WO 02/12242 (see, in particular, example 26 at page 249; this same compound is therein named as 3-amino-4,6-dihydro-pyrrolo[3,4-c]pyrazole-1,5-dicarboxylic acid 5-tert-butyl ester 1-ethyl ester).

By working in an analogous way, additional compounds of formula (II) wherein Q represents a lower alkyl group other than ethyl can be thus prepared as well.

The compounds of formula (III) and (VI), for instance those wherein Z and Z' represent a halogen atom, e.g. a chlorine atom, are either known or can be easily obtained from the corresponding known carboxylic acids, by working according to conventional methods.

Likewise, it is also clear to the person skilled in the art that if a compound of formula (I), prepared according to the above process comprehensive of any variant thereof, is obtained as an admixture of isomers, their separation into the single isomers of formula (I), carried out according to conventional techniques, is still within the scope of the present invention.

Pharmacology

The compounds of formula (I) are active as protein kinase inhibitors, more particularly as Aurora kinases inhibitors and are therefore useful, for instance, to restrict the unregulated proliferation of tumor cells.

In therapy, they may be used in the treatment of various tumors, such as those formerly reported, as well as in the treatment of other cell proliferative disorders such as psoriasis, vascular smooth cell proliferation associated with atherosclerosis and post-surgical stenosis and restenosis.

The inhibiting activity and the potency of selected compounds is determined through a method of assay based on the use of the SPA technology (Amersham Pharmacia Biotech). The assay consists of the transfer of radioactivity labelled phosphate moiety by the kinase to a biotinylated substrate. The resulting 33P-labelled biotinylated product is allowed to bind to streptavidin-coated SPA beads (biotin capacity 130 pmol/mg), and light emitted was measured in a scintillation counter.

Inhibition Assay of Aurora-2 Activity

Kinase reaction: 8 μM biotinylated peptide (4 repeats of LRRWSLG), 10 μM ATP (0.5 uCi $P^{33}\gamma$-ATP), 7.5 ng Aurora 2, inhibitor in a final volume of 30 μl buffer (HEPES 50 mM pH 7.0, $MgCl_2$ 10 mM, 1 mM DTT, 0.2 mg/ml BSA, 3 μM orthovanadate) were added to each well of a 96 U bottom well plate. After 60 minutes at room temperature incubation, reaction was stopped and biotinylated peptide captured by adding 100 μl of bead suspension.

Stratification: 100 μl of CsCl2 5 M were added to each well and let stand 4 hour before radioactivity was counted in the Top-Count instrument.

IC50 determination: inhibitors were tested at different concentrations ranging from 0.0015 to 10 μM. Experimental data were analyzed by the computer program GraphPad Prizm using the four parameter logistic equation:

y=bottom+(top−bottom)/(1+10^((log IC50−x)*slope))

where x is the logarithm of the inhibitor concentration, y is the response; y starts at bottom and goes to top with a sigmoid shape.

Ki Calculation:

Experimental method: Reaction was carried out in buffer (10 mM Tris, pH 7.5, 10 mM $MgCl_2$, 0.2 mg/ml BSA, 7.5 mM DTT) containing 3.7 nM enzyme, histone and ATP (constant ratio of cold/labeled ATP 1/3000). Reaction was stopped with EDTA and the substrate captured on phosphomembrane (Multiscreen 96 well plates from Millipore). After extensive washing, the multiscreen plates were read on a top counter. Control (time zero) for each ATP and histone concentrations was measured.

Experimental design: Reaction velocities are measured at four ATP, substrate (histone) and inhibitor concentrations. An 80-point concentration matrix was designed around the respective ATP and substrate Km values, and the inhibitor IC50 values (0.3, 1, 3, 9 fold the Km or IC50 values). A preliminary time course experiment in the absence of inhibitor and at the different ATP and substrate concentrations allows the selection of a single endpoint time (10 min) in the linear range of the reaction for the Ki determination experiment.

Kinetic parameter estimates: Kinetic parameters were estimated by simultaneous nonlinear least-square regression using [Eq.1] (competitive inhibitor respect to ATP, random mechanism) using the complete data set (80 points):

$$v = \frac{Vm \cdot A \cdot B}{\alpha \cdot Ka \cdot Kb + \alpha \cdot Ka \cdot B + a \cdot Kb \cdot A + A \cdot B + \alpha \cdot \frac{Ka}{Ki} \cdot I \cdot \left(Kb + \frac{B}{\beta}\right)} \quad [Eq. 1]$$

where A=[ATP], B=[Substrate], I=[inhibitor], Vm=maximum velocity, Ka, Kb, Ki the dissociation constants of ATP, substrate and inhibitor respectively α and β the cooperativity factor between substrate and ATP binding and substrate and inhibitor binding respectively.

The compounds of the invention were further tested in vitro to assess the anti-proliferative effect onto cell cultures and the inhibititory effect on the cell cycle.

In Vitro Cell Proliferation Assay

The human colon cancer cell line HCT-116 was seeded at 5000 cells/cm2 in 24 wells plate (Costar) using F12 medium (Gibco) supplemented with 10% FCS (EuroClone, Italy) 2 mM L-glutamine and 1% penicillin/streptomycin and maintained at 37° C., 5% $CO_2$ and 96% relative humidity. The following day, plates were treated in duplicates with 5 ul of an appropriate dilution of compounds starting from a 10 mM stock in DMSO. Two untreated control wells were included in each plate. After 72 hours of treatment, medium was withdrawn and cells detached from each well using 0.5 ml of 0.05% (w/v) Trypsin, 0.02% (w/v) EDTA (Gibco). Samples were diluted with 9.5 ml of Isoton (Coulter) and counted using a Multisizer 3 cell counter (Beckman Coulter). Data were evaluated as percent of the control wells:

% of CTR=(Treated−Blank)/(Control−Blank).

$IC_{50}$ values were calculated by LSW/Data Analysis using Microsoft Excel sigmoidal curve fitting.

In Vitro Cell Cycle Analysis

The human colon cancer cell line HCT-116 was seeded at 5000 cells/cm2 in 24 wells plate (Costar) and cultured as mentioned above. Cells in their exponential phase of growth were treated for 24 hours with different concentrations of compound. Also, culture medium supernatant was collected to avoid loss of detached apoptotic or mitotic cells. Thereafter, cells were washed using PBS and detached by 0.05% (w/v) trypsin, 0.02% (w/v) EDTA (Gibco). Trypsin activity was stopped using culture medium. Adherent and non-adherent cell fractions were pooled and centrifuged at 2000 rpm for 10 minutes. Cells were re-suspended in PBS and counted using a Multisizer 3 cell counter (Beckman Coulter). For fixation, ethanol was added (70%, v/v) and cells were kept at −20° C. overnight.

One million fixed cells were centrifuged at 2000 rpm for 5 minutes and washed with PBS and subsequently stained for 1 hour at room temperature in the dark by adding 200 □l: 25 □g/ml propidium iodide (Sigma) and 15 ug/ml RNAse A (Sigma), 0.001% (v/v) Nonidet P40 (Sigma) in sodium citrate (0.1% w/v, pH 7.5). Samples were analyzed by flow cytometry at 488 nm excitation (FACSCalibur, Beckton Dickinson) using Cell Quest 3.0 software (Beckton Dickinson). Typically 10000 events (activating doubles discriminate module DDM and gating only single cells) were collected and cell cycle profiles were recorded using CellQuest (Verity Software). Cell Cycle distribution of the population was calculated using a modified model in Modfit 3.1 software (Verity Software) and expressed in % G0/G1, S, G2/M and polyploidy.

Given the above assays, the compounds of formula (I) of the invention resulted to possess a remarkable protein kinase inhibitory activity, e.g. Aurora-2 inhibitory activity. See, as an example, the following table I reporting the experimental data of four representative compounds of the invention being tested as Aurora-2 kinase inhibitors ($IC_{50}$ nM), for their cell antiproliferative effect ($IC_{50}$ nM), and for their capability to exert cell cycle blocking and induce polyploidy (% of G2/M+ polyploidy at 200 nM).

Interestingly, these same compounds were tested in comparison to a structurally very close prior art compound, herewith defined as Reference compound, which is specifically disclosed in the aforementioned WO 02/12242—see page 160, lines 5-7 of the same; the Reference compound was therein named as N-{5-phenylacetyl-4,6-dihydropyrrolo[3,4-c]pyrazol-3-yl}-4-(4-methylpiperazino)benzamide.

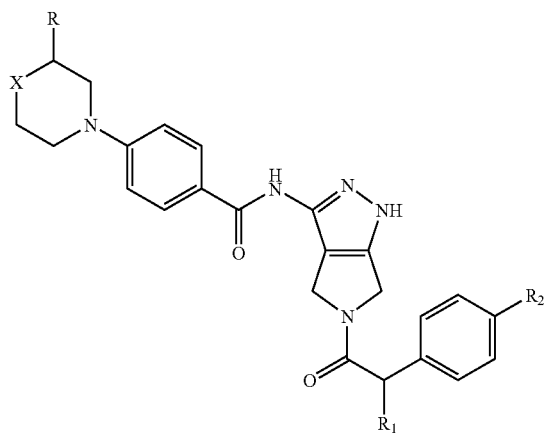

(I)

Reference Compound (R=$R_1$=$R_2$=H; X=NMe)
N-{5-phenylacetyl-4,6-dihydropyrrolo[3,4-c]pyrazol-3-yl}-4-(4-methylpiperazino)benzamide;

Compound (1) (R=$R_2$=H; $R_1$=OMe; X=NMe)
N-{5-[(2R)-2-methoxy-2-phenylethanoyl]-1,4,5,6-tetrahydropyrrolo[3,4-c]pyrazol-3-yl}-4-(4-methylpiperazin-1-yl)benzamide;

Compound (11) (R=$R_2$=H; $R_1$=Me; X=NMe)
N-{5-[(2R)-2-methyl-2-phenylethanoyl]-1,4,5,6-tetrahydropyrrolo[3,4-c]pyrazol-3-yl}-4-(4-methylpiperazin-1-yl)benzamide;

Compound (6) (R=$R_2$=H; $R_1$=OMe; X=$CH_2$)
N-{5-[(2R)-2-methoxy-2-phenylethanoyl]-1,4,5,6-tetrahydropyrrolo[3,4-c]pyrazol-3-yl}-4-piperidin-1-ylbenzamide;

Compound (5) (R=Me; $R_1$=OMe; $R_2$=H; X=NMe)
4-(3,4-dimethylpiperazin-1-yl)-N-{5-[(2R)-2-methoxy-2-phenylethanoyl]-1,4,5,6-tetrahydropyrrolo[3,4-c]pyrazol-3-yl}benzamide.

TABLE I

| Compound | Aurora-2 inhibition $IC_{50}$ (nM) | Cell Antiproliferation $IC_{50}$ (nM) | Cell Cycle block (% G2/M + polyploidy at 200 nM) |
|---|---|---|---|
| Reference compound | 140 | 220 | 33 |
| none | — | — | 19 |
| (1) | 16 | 31 | 90 |
| (11) | 63 | 17 | 90 |
| (6) | 37 | 30 | 90 |
| (5) | 18 | 50 | 90 |

Surprisingly, the Aurora-2 inhibitory activity of the compounds of the invention resulted to be constantly and markedly superior that that of the Reference compound.

In addition, those same compounds resulted to possess a cell antiproliferative effect together with the capability to block the cell cycle and induce polyploidy, significantly superior than that of the Reference compound being tested in the same conditions.

From all of the above, the novel compounds of formula (I) of the invention appear to be endowed with a biological profile, considered as a whole, which is unexpectedly superior thant that of the closest prior art of WO 02/12242 and, hence, are particularly advantageous, in therapy, against proliferative disorders associated with an altered Aurora-2 kinase activity.

The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight, conditions of the patient and administration route.

For example, a suitable dosage adopted for oral administration of a compound of formula (I) may range from about 10 to about 500 mg per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form.

For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions.

As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol.

The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

With the aim to better illustrate the present invention, without posing any limitation to it, the following examples are now given.

EXAMPLES

General Methods

Flash chromatography was performed on silica gel (Merck grade 9385, 60 Å). HPLC/MS was performed on a Waters X Terra RP 18 (4.6×50 mm, 3.5 μm) column using a Waters 2790 HPLC system equipped with a 996 Waters PDA detector and a Micromass mod. ZQ single quadrupole mass spectrometer, equipped with an electrospray (ESI) ion source. Mobile phase A was ammonium acetate 5 mM buffer (pH 5.5 with acetic acid/acetonitrile 95:5), and Mobile phase B was $H_2O$/acetonitrile (5:95). Gradient from 10 to 90% B in 8 minutes, hold 90% B 2 min. UV detection at 220 nm and 254 nm. Flow rate 1 ml/min. Injection volume 10 μl. Full scan, mass range from 100 to 800 amu. Capillary voltage was 2.5 KV; Source temp. was 120° C.; Cone was 10 V. Retention Times (HPLC r.t.) are given in minutes at 220 nm or 254 nm. Mass are given as m/z ratio. 1H-NMR spectroscopy was performed on a Mercury VX 400 operating at 400.45 MHz equipped with a 5 mm double resonance probe (1H {15N-31P} ID_PFG Varian).

Example 1

Preparation of 5-tert-butyl 1-ethyl 3-amino-4,6-dihydropyrrolo[3,4-c]pyrazole-1,5-dicarboxylate A solution of ethyl chlorocarbonate (8.9 ml, 93 mmol) in tetrahydrofuran (THF, 250 ml) was slowly added to a mixture of tert-butyl 3-amino-4,6-dihydropyrrolo[3,4-c]pyrazole-5(1H)-carboxylate (20 g, 89 mmol) and diisopropylethylamine (DIEA, 92 ml, 528 mmol) in THF (500 ml) at 0-5° C. The reaction was kept at the same temperature for two hours then allowed to reach room temperature and stirred overnight. The obtained mixture was evaporated to dryness under vacuum, and the resulting residue extracted with ethyl acetate (AcOEt) and water. The organic layer was separated, dried over sodium sulfate and evaporated to dryness. The mixture was purified by flash-chromatography (eluent: ethyl acetate/cyclohexane 4/6 to 7/3) to give 19 g of the title compound as a white solid. $[M+H]^+$ 297

Example 2

Preparation of 5-tert-butyl 1-ethyl 3-{[4-(4-methylpiperazin-1-yl)benzoyl]amino}-4,6-dihydropyrrolo[3,4c]pyrazole-1,5-dicarboxylate Oxalyl chloride (23.2 ml, 265 mmol) was added to a suspension of 4-(4-methyl-1-piperazinyl)-benzoic acid (11.7 g, 53 mmol) in dichloromethane (DCM, 320 ml) and dimethylformamide (DMF, 0.52 ml). After refluxing the mixture for 6.5 hours, volatiles were carefully removed under reduced pressure (taking up the residue three times with toluene).

The resulting 4-methylpiperazino-benzoyl chloride di-hydrochloride was added portionwise to a solution of 5-tert-butyl 1-ethyl 3-amino-4,6-dihydropyrrolo[3,4-c]pyrazole-1,5-dicarboxylate (13.1 g, 44.3 mmol) in dry THF (620 ml) and DIEA (54.4 ml, 0.32 mol) under stirring at room temperature. The resulting suspension was stirred 16 hours at room temperature and 1 hour at 40° C.

After solvent removal under reduced pressure, the residue was taken up with AcOEt (600 ml) and the organic layer washed with aqueous sodium carbonate (200 ml), brine, (200 ml) and dried over sodium sulfate.

Solvent was evaporated, and the residue was triturated with a mixture of diethyl ether ($Et_2O$, 135 ml) and AcOEt (15 ml), filtered, dried under vacuum at 40° C. to give 20 g of the title compound as a white powder $[M+H]^+$ 499.

By operating in an analogous way and by reacting 5-tert-butyl 1-ethyl 3-amino-4,6-dihydropyrrolo[3,4-c]pyrazole-1,5-dicarboxylate with the appropriate acyl chloride derivative, the following compounds were prepared:

5-tert-butyl 1-ethyl 3-{[4-(4-ethylpiperazin-1-yl)benzoyl]amino}-4,6-dihydropyrrolo[3,4-c]pyrazole-1,5-dicarboxylate; $[M+H]^+$ 513.

5-tert-butyl 1-ethyl 3-{[4-(4-isopropylpiperazin-1-yl)benzoyl]amino}-4,6-dihydropyrrolo[3,4-(5)c]pyrazole-1,5-dicarboxylate; [M+H]⁺ 527.

5-tert-butyl 1-ethyl 3-{[4-(4-cyclopropylpiperazin-1-yl)benzoyl]amino}-4,6-dihydropyrrolo[3,4-c]pyrazole-1,5-dicarboxylate; [M+H]⁺ 525.

5-tert-butyl 1-ethyl 3-{[4-(3,4-dimethylpiperazin-1-yl)benzoyl]amino}-4,6-dihydropyrrolo[3,4-c]pyrazole-1,5-dicarboxylate; [M+H]⁺ 513.

5-tert-butyl 1-ethyl 3-[(4-piperidin-1-ylbenzoyl)amino]-4,6-dihydropyrrolo[3,4-c]pyrazole-1,5-dicarboxylate; [M+H]⁺ 484.

5-tert-butyl 1-ethyl 3-{[4-(4-fluoropiperidin-1-yl)benzoyl]amino}-4,6-dihydropyrrolo[3,4-c]pyrazole-1,5-dicarboxylate; [M+H]⁺ 502.

5-tert-butyl 1-ethyl 3-[(4-morpholin-4-ylbenzoyl)amino]-4,6-dihydropyrrolo[3,4-c]pyrazole-1,5-dicarboxylate; [M+H]⁺ 486.

5-tert-butyl 1-ethyl 3-{[4-(4-tert-butylpiperazin-1-yl)benzoyl]amino}-4,6-dihydropyrrolo[3,4-(5)c]pyrazole-1,5-dicarboxylate; [M+H]⁺ 541.

Example 3

Preparation of ethyl 3-{[4-(4-methylpiperazin-1-yl)benzoyl]amino}-5,6-dihydropyrrolo[3,4-c]pyrazole-1(4H)-carboxylate trihydrochloride A 4N solution of hydrochloric acid in dioxane (122 ml, 488 mmol) was added dropwise to a stirred solution of 5-tert-butyl 1-ethyl 3-{[4-(4-methylpiperazin-1-yl)benzoyl]amino}-4,6-dihydropyrrolo[3,4-c]pyrazole-1,5-dicarboxylate (19.5 g, 39.2 mmol), as prepared in Example 2, in dry DCM (240 ml); precipitation of a white solid occurred almost immediately. The resulting mixture was stirred at room temperature for 24 hours; after dilution with Et₂0 (100 ml), the solid was filtered, extensively washed with Et₂0, and dried under vacuum at 50° C. to give 20.1 g of the title compound, used in the next step without further purification. [M+H]⁺ 399.

1H-NMR (DMSO-d6) δ ppm: 1.4 (t, 3H); 2.8 (d, 3H); 3.2 (m, 4H); 3.5 (m, 2H); 4.1 (m, 2H); 4.4 (q, 2H); 4.6 (m, 4H); 7.1-8.0 (m, 4H); 10.3 (bs, 2H); 10.7 (bs, 1H); 11.4 (s, 1H).

By operating as above reported and by starting from the suitable intermediate, the following compounds were analogously prepared:

ethyl 3-{[4-(4-ethylpiperazin-1-yl)benzoyl]amino}-5,6-dihydropyrrolo[3,4-c]pyrazole-1(4H)-carboxylate trihydrochloride; [M+H]⁺ 413.

ethyl 3-{[4-(4-isopropylpiperazin-1-yl)benzoyl]amino}-5,6-dihydropyrrolo[3,4-c]pyrazole-1 (4H)-carboxylate trihydrochloride; [M+H]⁺ 427.

ethyl 3-{[4-(4-cyclopropylpiperazin-1-yl)benzoyl]amino}-5,6-dihydropyrrolo[3,4-c]pyrazole-1(4H)-carboxylate trihydrochloride; [M+H]⁺ 425.

ethyl 3-{[4-(3,4-dimethylpiperazin-1-yl)benzoyl]amino}-5,6-dihydropyrrolo[3,4-c]pyrazole-1(4H)-carboxylate trihydrochloride; [M+H]⁺ 413.

ethyl 3-[(4-piperidin-1-ylbenzoyl)amino]-5,6-dihydropyrrolo[3,4-c]pyrazole-1 (4H)-carboxylate; [M+H]⁺ 384.

ethyl 3-{[4-(4-fluoropiperidin-1-yl)benzoyl]amino}-5,6-dihydropyrrolo[3,4-c]pyrazole-1 (4H)-carboxylate trihydrochloride; [M+H]⁺ 402.

ethyl 3-{[4-(4-morfolin-4-yl)benzoyl]amino}-5,6-dihydropyrrolo[3,4-c]pyrazole-1(4H)-carboxylate trihydrochloride; [M+H]⁺ 386.

ethyl 3-{[4-(4-tert-butylpiperazin-1-yl)benzoyl]amino}-5,6-dihydropyrrolo[3,4-c]pyrazole-1(4H)-carboxylate trihydrochloride; [M+H]⁺ 441.

Example 4

Preparation of ethyl 5-[(2R)-2-methoxy-2-phenylethanoyl]-3-{[4-(4-methylpiperazin-1-yl)benzoyl]amino}-5,6-dihydropyrrolo[3,4-c]pyrazole-1(4H)-carboxylate Oxalyl chloride (10.1.2 ml, 115 mmol) was added to a solution of R-(−)-α-methoxyphenylacetic acid (1.91 g, 11.5 mmol) in DCM (90 ml) and DMF (0.50 ml). After stirring the mixture at room temperature for 16 hours, volatiles were carefully removed under reduced pressure.

A solution of the resulting R-(−)-α-methoxyphenylacetyl chloride in DCM (20 ml) was added dropwise to a solution of ethyl 3-{[4-(4-methylpiperazin-1-yl)benzoyl]amino}-5,6-dihydropyrrolo[3,4-c]pyrazole-1(4H)-carboxylate trihydrochloride (4.5 g, 8.9 mmol) in DCM (400 ml) and DIEA (11.8 ml, 69 mmol) under stirring at room temperature. The resulting solution was stirred for 20 hours at room temperature.

The reaction mixture was then washed with aqueous sodium carbonate (200 ml), brine, (200 ml) and dried over sodium sulfate. Solvent was evaporated, and the residue was triturated with a mixture of Et₂0 (100 ml) and AcOEt (10 ml), filtered, and dried under vacuum at 40° C. to give 3.94 g of the title compound as a white powder used in the following step without further purification. [M+H]⁺ 547;

1H-NMR (DMSO-d6) δ ppm: 1.3 (t, 3H); 2.3 (d, 3H); 2.6 (m, 4H); 3.3-3.4 (m, 7H); 4.3 (q, 2H); 4.6-4.9 (m, 4H); 5.1 (d, 1H) 7.0-8.0 (m, 9H); 11.1 (d, 1H).

By operating as above reported and by starting from the suitable acyl chloride derivative, the following compounds were analogously prepared:

ethyl 5-[(2R)-2-methoxy-2-phenylethanoyl]-3-{[4-(4-ethylpiperazin-1-yl)benzoyl]amino}-5,6-dihydropyrrolo[3,4-c]pyrazole-1(4H)-carboxylate; [M+H]⁺ 561.

ethyl 5-[(2R)-2-methoxy-2-phenylethanoyl]-3-{[4-(4-isopropylpiperazin-1-yl)benzoyl]amino}-5,6-dihydropyrrolo[3,4-c]pyrazole-1(4H)-carboxylate; [M+H]⁺ 575.

ethyl 5-[(2R)-2-methoxy-2-phenylethanoyl]-3-{[4-(4-cyclopropylpiperazin-1-yl)benzoyl]amino}-5,6-dihydropyrrolo[3,4-c]pyrazole-1(4H)-carboxylate; [M+H]⁺ 573.

ethyl 3-{[4-(3,4-dimethylpiperazin-1-yl)benzoyl]amino}-5-[(2R)-2-methoxy-2-phenylethanoyl]-5,6-dihydropyrrolo[3,4-c]pyrazole-1(4H)-carboxylate; [M+H]⁺ 561.

ethyl 5-[(2R)-2-methoxy-2-phenylethanoyl]-3-[(4-piperidin-1-ylbenzoyl)amino]-5,6-dihydropyrrolo[3,4-c]pyrazole-1(4H)-carboxylate; [M+H]⁺ 532.

ethyl 3-{[4-(4-fluoropiperidin-1-yl)benzoyl]amino}-5-[(2R)-2-methoxy-2-phenylethanoyl]-5,6-dihydropyrrolo[3,4-c]pyrazole-1(4H)-carboxylate; [M+H]⁺ 550.

ethyl 5-[(2R)-2-methoxy-2-phenylethanoyl]-3-[(4-morpholin-4-ylbenzoyl)amino]-5,6-dihydropyrrolo[3,4-c]pyrazole-1(4H)-carboxylate; [M+H]⁺ 534.

ethyl 3-{[4-(4-tert-butylpiperazin-1-yl)benzoyl]amino}-5-[(2R)-2-methoxy-2-phenylethanoyl]-5,6-dihydropyrrolo[3,4-c]pyrazole-1(4H)-carboxylate; [M+H]⁺ 589.

ethyl 5-[(2R)-2-methyl-2-phenylethanoyl]-3-{[4-(4-ethylpiperazin-1-yl)benzoyl]amino}-5,6-dihydropyrrolo[3,4-c]pyrazole-1(4H)-carboxylate; [M+H]⁺ 545.

ethyl 5-[(2R)-2-methyl-2-phenylethanoyl]-3-{[4-(4-isopropylpiperazin-1-yl)benzoyl]amino}-5,6-dihydropyrrolo[3,4-c]pyrazole-1(4H)-carboxylate; [M+H]⁺ 559.

ethyl 5-[(2R)-2-methyl-2-phenylethanoyl]-3-{[4-(4-cyclopropylpiperazin-1-yl)benzoyl]amino}-5,6-dihydropyrrolo[3,4-c]pyrazole-1(4H)-carboxylate; [M+H]$^+$ 557.

ethyl 3-{[4-(3,4-dimethylpiperazin-1-yl)benzoyl]amino}-5-[(2R)-2-methyl-2-phenylethanoyl]-5,6-dihydropyrrolo[3,4-c]pyrazole-1(4H)-carboxylate; [M+H]$^+$ 545.

ethyl 5-[(2R)-2-methyl-2-phenylethanoyl]-3-[(4-piperidin-1-ylbenzoyl)amino]-5,6-dihydropyrrolo[3,4-c]pyrazole-1(4H)-carboxylate; [M+H]$^+$ 516.

ethyl 3-{[4-(4-fluoropiperidin-1-yl)benzoyl]amino}-5-[(2R)-2-methyl-2-phenylethanoyl]-5,6-dihydropyrrolo[3,4-c]pyrazole-1(4H)-carboxylate; [M+H]$^+$ 534.

ethyl 5-[(2R)-2-methyl-2-phenylethanoyl]-3-[(4-morpholin-4-ylbenzoyl)amino]-5,6-dihydropyrrolo[3,4-c]pyrazole-1(4H)-carboxylate; [M+H]$^+$ 518.

ethyl 3-{[4-(4-tert-butylpiperazin-1-yl)benzoyl]amino}-5-[(2R)-2-methyl-2-phenylethanoyl]-5,6-dihydropyrrolo[3,4-c]pyrazole-1(4H)-carboxylate; [M+H]$^+$ 573.

ethyl 5-[(2R)-2-hydroxy-2-phenylethanoyl]-3-{[4-(4-methylpiperazin-1-yl)benzoyl]amino}-5,6-dihydropyrrolo[3,4-c]pyrazole-1(4H)-carboxylate; [M+H]$^+$ 533.

Example 5

Preparation of N-{5-[(2R)-2-methoxy-2-phenylethanoyl]-1,4,5,6-tetrahydropyrrolo[3,4-c]pyrazol-3-yl}-4-(4-methylpiperazin-1-yl)benzamide (1)

A solution of ethyl 5-[(2R)-2-methoxy-2-phenylethanoyl]-3-{[4-(4-methylpiperazin-1-yl)benzoyl]amino}-5,6-dihydropyrrolo[3,4-c]pyrazole-1(4H)-carboxylate (3.94 g, 7.2 mmol) in methanol (MeOH, 130 ml) and triethylamine (Et$_3$N, 13 ml) was stirred at room temperature for 16 hours (some precipitation occurred). The solid was separated and washed with Et$_2$O, to give 1.6 g of the title compound. Solution was evaporated up to few milliliters, and a second fraction of solid product was separated (1.62 g). The two fractions were joined and analyzed by LC-MS (purity around 90% 254 and 220 nM). After chromatographic purification (short silica gel column, DCM/MeOH 45:5) 2.83 g (83%) of the title compound were obtained as a white solid. M.p 289° C.; [M+H]$^+$ 475;

1H-NMR (DMSO-d6) δ ppm: 2.21 (s, 3H); 2.43 (m, 4H); 3.29 (m, 7H); 4.20-4.90 (m, 4H); 5.09 (s, 1H) 6.80-8.00 (m, 9H); 10.6 (br, 1H); 12.09 (br, 1H).

By operating in an analogous way, through basic hydrolysis of the compounds of example 4, the following compounds were prepared:

(2) N-{5-[(2R)-2-methoxy-2-phenylethanoyl]-1,4,5,6-tetrahydropyrrolo[3,4-c]pyrazol-3-yl}-4-(4-ethylpiperazin-1-yl)benzamide; [M+H]$^+$ 489;

1H-NMR (DMSO-d6) δ ppm: 1.1 (t, 3H); 2.3-2.7 (m, 6H); 3.2-3.4 (m, 7H); 4.3-6.0 (m, 4H); 5.1 (d, 1H) 6.9-8.0 (m, 9H); 10.6 (bs, 1H); 12.1 (br, 1H).

(3) N-{5-[(2R)-2-methoxy-2-phenylethanoyl]-1,4,5,6-tetrahydropyrrolo[3,4-c]pyrazol-3-yl}-4-(4-isopropylpiperazin-1-yl)benzamide; [M+H]$^+$ 503;

1H-NMR (DMSO-d6) δ ppm: 1.3-1.3 (dd, 6H); 3.3-3.4 (m, 9H); 4.6-4.9 (m, 4H); 5.1 (d, 1H); 7.0-8.0 (m, 9H); 10.7 (bs, 1H); 12.3 (bs, 1H).

(4) N-{5-[(2R)-2-methoxy-2-phenylethanoyl]-1,4,5,6-tetrahydropyrrolo[3,4-c]pyrazol-3-yl}-4-(4-cyclopropylpiperazin-1-yl)benzamide; [M+H]$^+$ 501;

1H-NMR (DMSO-d6) δ ppm: 0.3-0.5 (m, 4H); 3.2-3.4 (m, 7H); 3.2-5.0 (m, 4H); 5.1 (d, 1H); 6.8-8.2 (m, 9H); 10.5-10.7 (br, 1H); 12.0-12.4 (br, 1H).

(5) 4-(3,4-dimethylpiperazin-1-yl)-N-{5-[(2R)-2-methoxy-2-phenylethanoyl]-1,4,5,6-tetrahydropyrrolo[3,4-c]pyrazol-3-yl}benzamide; [M+H]$^+$ 489;

1H-NMR (DMSO-d6) δ ppm: 1.0-1.1 (m, 3H); 2.24 (s, 3H); 3.3-3.5 (m, 7H); 4.3-5.0 (m, 4H); 5.1 (d, 1H); 6.9-8.0 (m, 9H); 10.6 (bs, 1H); 11.9-12.6 (br, 1H).

(6) N-{5-[(2R)-2-methoxy-2-phenylethanoyl]-1,4,5,6-tetrahydropyrrolo[3,4-c]pyrazol-3-yl}-4-piperidin-1-ylbenzamide; [M+H]$^+$ 460;

1H-NMR (DMSO-d6) δ ppm: 1.5-1.7 (m, 6H); 3.2-3.4 (m, 7H); 4.3-4.9 (m, 4H); 5.1 (d, 1H); 6.9-8.0 (m, 9H); 10.4-10.7 (br, 1H).

(7) 4-(4-fluoropiperidin-1-yl)-N-{5-[(2R)-2-methoxy-2-phenylethanoyl]-1,4,5,6-tetrahydropyrrolo[3,4-c]pyrazol-3-yl}benzamide; [M+H]$^+$ 478;

1H-NMR (DMSO-d6) δ ppm: 1.65-2.1 (m, 4H); 3.15-3.6 (m, 7H); 4.35-5.0 (m, 5H); 5.1 (d, 1H); 6.9-8.0 (m, 9H); 10.4-10.7 (br, 1H).

(8) N-{5-[(2R)-2-methoxy-2-phenylethanoyl]-1,4,5,6-tetrahydropyrrolo[3,4-c]pyrazol-3-yl}-4-morpholin-4-ylbenzamide; [M+H]$^+$ 462;

1H-NMR (DMSO-d6) δ ppm: 3.15-3.5 (m, 7H); 3.7-3.8 (m, 4H); 4.3-4.9 (m, H); 5.1 (d, 1H); 6.9-8.0 (m, 9H); 10.4-10.7 (br, 1H).

(9) 4-(4-tert-butylpiperazin-1-yl)-N-{5-[(2R)-2-methoxy-2-phenylethanoyl]-1,4,5,6-tetrahydropyrrolo[3,4-c]pyrazol-3-yl}benzamide; [M+H]$^+$ 517.

(10) N-{5-[(2R)-2-hydroxy-2-phenylethanoyl]-1,4,5,6-tetrahydropyrrolo[3,4-c]pyrazol-3-yl}-4-(4-methylpiperazin-1-yl)benzamide; [M+H]$^+$ 461;

1H-NMR (DMSO-d6) δ ppm: 2.3 (s, 3H); 2.45-2.65 (m, 4H); 3.2-3.4 (m, 4H); 4.1-4.9 (m, 4H); 5.69 (d, 1H); 6.9-8.0 (m, 9H); 10.4-10.7 (br, 1H); 11.5-12.9 (br, 1H).

(11) N-{5-[(2R)-2-methyl-2-phenylethanoyl]-1,4,5,6-tetrahydropyrrolo[3,4-c]pyrazol-3-yl}-4-(4-methylpiperazin-1-yl)benzamide; [M+H]$^+$ 459;

1H-NMR (DMSO-d6) δ ppm: 1.33 (d, 3H); 2.21 (s, 3H); 3.85-5.0 (m, 5H); 4.2-4.9 (m, 4H); 5.1 (s, 1H) 6.8-8.0 (m, 9H); 10.3-10.7 (br, 1H); 11.8-12.5 (br, 1H).

(12) N-{5-[(2R)-2-methyl-2-phenylethanoyl]-1,4,5,6-tetrahydropyrrolo[3,4-c]pyrazol-3-yl}-4-(4-ethylpiperazin-1-yl)benzamide; [M+H]$^+$ 473;

1H-NMR (DMSO-d6) δ ppm: 1.06 (t, 3H); 1.36 (d, 3H); 2.41 (q, 2H); 2.47-2.6 (m, 4H); 3.2-3.4 (m, 4H); 3.9-5.0 (m, 5H); 6.9-8.0 (m, 9H); 10.5 (bs, 1H); 11.9-12.5 (br, 1H).

(13) N-{5-[(2R)-2-methyl-2-phenylethanoyl]-1,4,5,6-tetrahydropyrrolo[3,4-c]pyrazol-3-yl}-4(4-isopropylpiperazin-1-yl)benzamide; [M+H]$^+$ 487;

(14) N-{5-[(2R)-2-methyl-2-phenylethanoyl]-1,4,5,6-tetrahydropyrrolo[3,4c]pyrazol-3-yl}-4-(4-cyclopropylpiperazin-1-yl)benzamide; [M+H]$^+$ 485;

(15) 4-(3,4-dimethylpiperazin-1-yl)-N-{5-[(2R)-2-phenylpropanoyl]-1,4,5,6-tetrahydropyrrolo[3,4-c]pyrazol-3-yl}benzamide; [M+H]$^+$ 473;

(16) N-{5-[(2R)-2-phenylpropanoyl]-1,4,5,6-tetrahydropyrrolo[3,4-c]pyrazol-3-yl}-4-piperidin-1-ylbenzamide; [M+H]$^+$ 444;

1H-NMR (DMSO-d6) δ ppm: 1.37 (d, 3H); 1.6 (s, 6H); 3.2-3.4 (m, 4H); 3.90-4.05 (m, 1H); 4.1-4.9 (m, 4H); 6.9-8.0 (m, 9H); 10.4-10.7 (br, 1H).

(17) 4-(4-fluoropiperidin-1-yl)-N-{5-[(2R)-2-methyl-2-phenylethanoyl]-1,4,5,6-tetrahydropyrrolo[3,4-c]pyrazol-3-yl}benzamide; [M+H]$^+$ 462;

1H-NMR (DMSO-d6) δ ppm: 1.37 (d, 3H); 1.65-2.05 (m, 4H); 3.15-3.6 (m, 7H); 3.2-3.4 (m, 4H); 3.85-4.07 (m, 1H);

4.1-5.05 (m, 5H); 5.1 (d, 1H); 6.9-8.0 (m, 9H); 10.4-10.7 (br, 1H).

(18) N-{5-[(2R)-2-methyl-2-phenylethanoyl]-1,4,5,6-tetrahydropyrrolo[3,4-c]pyrazol-3-yl}-4-morpholin-4-yl-benzamide; [M+H]$^+$ 446;

1H-NMR (DMSO-d6) δ ppm: 1.37 (d, 3H); 3.2-3.4 (m, 4H); 3.7-3.85 (m, 4H); 3.9-4.1 (m, 1H); 4.1-4.95 (m, 4H); 6.9-8.0 (m, 9H); 10.4-10.7 (br, 1H).

(19) 4-(4-tert-butylpiperazin-1-yl)-N-{5-[(2R)-2-phenylpropanoyl]-1,4,5,6-tetrahydropyrrolo[3,4-c]pyrazol-3-yl}benzamide; [M+H]$^+$ 501.

The invention claimed is:

1. A method for treating cell proliferative disorders caused by and/or associated with an altered protein kinase activity which comprises administering to a mammal in need thereof an effective amount of a compound of formula (I)

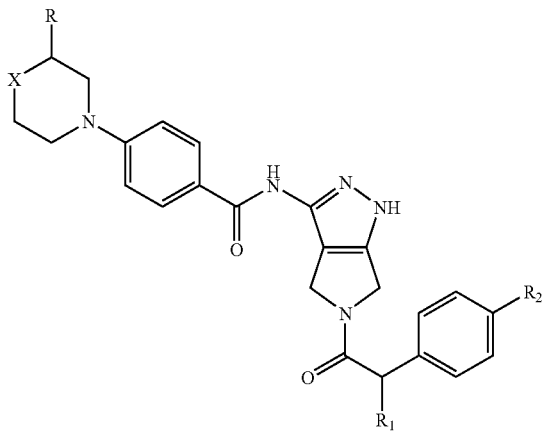

(I)

wherein
R is hydrogen or methyl;
$R_1$ is an alkoxy group;
$R_2$ is a hydrogen or halogen atom;
X is a divalent group selected from methylene (—CH$_2$—) or fluoromethylene (—CHF—), or it is a heteroatom or heteroatomic group selected from oxygen (—O—) or nitrogen (—NR'—) wherein R' is a hydrogen atom, a straight or branched $C_1$-$C_4$ alkyl group or a $C_3$-$C_6$ cycloalkyl group;
or a pharmaceutically acceptable salt thereof;
wherein said cell proliferative disorders are selected from the group consisting of benign prostate hyperplasia, familial adenomatosis polyposis, neuro-fibromatosis, melanoma, teratocarcinoma, xeroderma pigmentosum, keratoxanthoma, Kaposi's sarcoma, colon cancer, lung cancer, osterosarcoma, hematopoietic tumors of myeloid or lymphoid lineage, mesothelioma, kidney cancer, breast cancer, ovary cancer, pancreas cancer, prostate cancer, thyroid, and cervix cancer.

2. The method according to claim 1 for treating cell proliferative disorders caused by and/or associated with an altered Aurora kinase activity.

3. The method according to claim 2 wherein the Aurora kinase is Aurora 2.

4. The method according to claim 1 further comprising subjecting the mammal in need thereof to a radiation therapy or chemotherapy regimen in combination with at least one cytostatic or cytotoxic agent.

5. The method according to claim 1 wherein the mammal in need thereof is a human.

6. A method for inhibiting Aurora 2 kinase activity which comprises contacting the said kinase with an effective amount of a compound as defined in claim 1 in vitro.

* * * * *